US00PP33907P3

(12) United States Plant Patent
Schoone

(10) Patent No.: US PP33,907 P3
(45) Date of Patent: Jan. 25, 2022

(54) ***PHALAENOPSIS* PLANT NAMED 'CLIFFHANGER'**

(50) Latin Name: *Phalaenopsis hybrida*
Varietal Denomination: Cliffhanger

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 17/339,950

(22) Filed: Jun. 5, 2021

(65) Prior Publication Data

US 2021/0385985 P1 Dec. 9, 2021

Related U.S. Application Data

(60) Provisional application No. 62/705,003, filed on Jun. 6, 2020.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62
See application file for complete search history.

(56) References Cited

PUBLICATIONS

Trademark to 'Cliffhanger', U.S. Appl. No. 88/900,000, filed May 4, 2020, abandoned Jun. 17, 2021.*

* cited by examiner

*Primary Examiner* — Anne Marie Grunberg
(74) *Attorney, Agent, or Firm* — C. Anne Whealy

(57) ABSTRACT

A new and distinct cultivar of *Phalaenopsis* plant named 'Cliffhanger', characterized by its upright plant habit; moderately vigorous to vigorous growth habit; strong flowering stems; strong leaves; freely flowering habit with typically two inflorescences per plant, each inflorescence with numerous flowers; large white-colored flowers with yellow-colored labella; and good postproduction longevity.

2 Drawing Sheets

Figure 1:
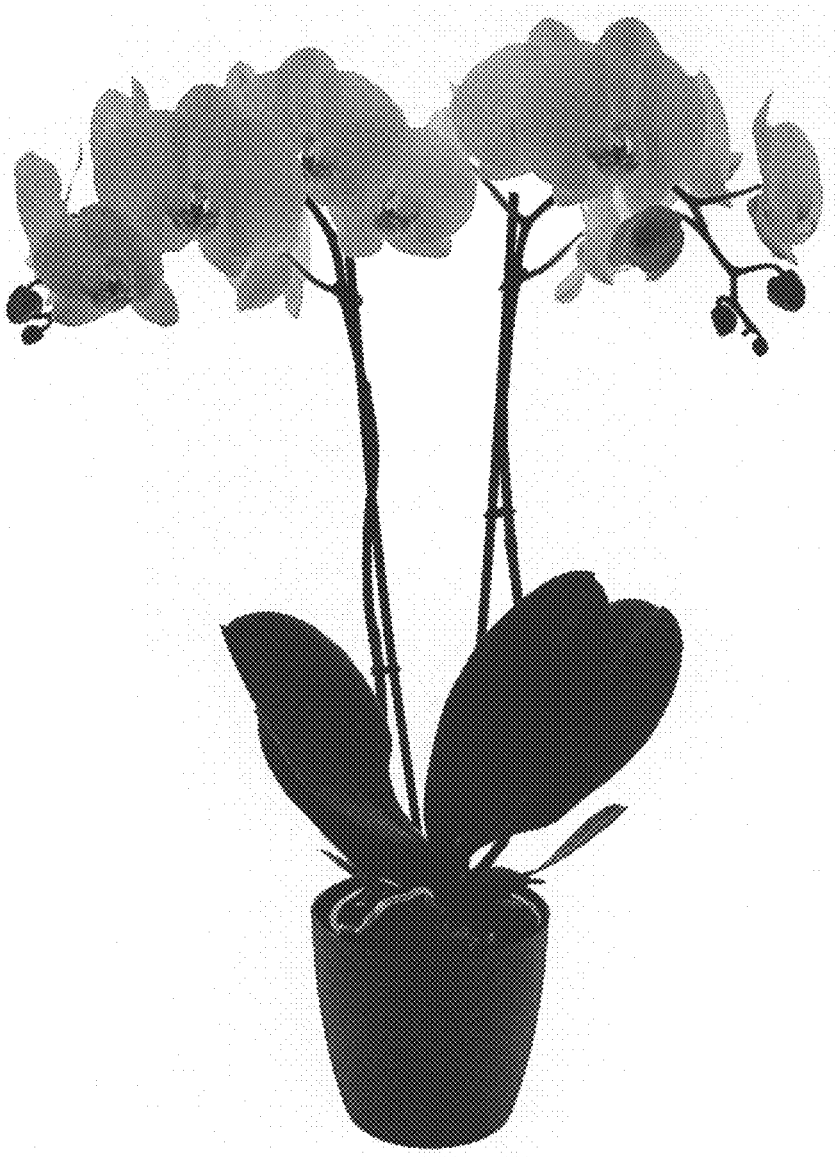

Botanical designation: *Phalaenopsis hybrida.*
Cultivar denomination: 'CLIFFHANGER'.

STATEMENT REGARDING PRIOR DISCLOSURES BY INVENTOR and APPLICANT/ASSIGNEE

An European Community Plant Breeder's Rights application for the instant plant was filed by the Applicant/Assignee of the instant application, Floricultura B.V. of Heemskerk, The Netherlands on Sep. 17, 2020, application number 2020/2182. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Cliffhanger'.

The new *Phalaenopsis* plant is a product of a planned breeding program conducted by the Inventor in Den Hoorn and Heemskerk, The Netherlands. The objective of the breeding program is to develop new fast-growing and freely flowering *Phalaenopsis* plants with good leaf shape and large flowers with unique and attractive patterns and coloration.

The new *Phalaenopsis* plant originated from a cross-pollination in January, 2011 in Den Hoorn, The Netherlands of a proprietary selection of *Phalaenopsis hybrida* identified as code number 1006336, not patented, as the female, or seed, parent with a proprietary selection of *Phalaenopsis hybrida* identified as code number 1006337, not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in June, 2017.

Asexual reproduction of the new *Phalaenopsis* plant by in vitro meristem propagation in a controlled environment in Assendelft, The Netherlands since June, 2018 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Cliffhanger'. These characteristics in combination distinguish 'Cliffhanger' as a new and distinct *Phalaenopsis* plant:

1. Upright plant habit.
2. Moderately vigorous to vigorous growth habit.
3. Strong flowering stems.
4. Strong leaves.
5. Freely flowering habit with typically two inflorescences per plant, each inflorescence with numerous flowers.
6. Large white-colored flowers with yellow-colored labella.
7. Good postproduction longevity.

Plants of the new *Phalaenopsis* can be compared to plants of the female parent selection. Plants of the new *Phalaenopsis* differ primarily from plants of the female parent selection in flower shape as petals of plants of the new *Phalaenopsis* are free to touching whereas petals of plants of the female parent selection are free and not touching. In addition, sepals of plants of the new *Phalaenopsis* are overlapping whereas sepals of plants of the female parent selection are free and not overlapping.

Plants of the new *Phalaenopsis* can be compared to plants of the male parent selection. Plants of the new *Phalaenopsis* differ primarily from plants of the male parent selection in the following characteristics:

1. Plants of the new *Phalaenopsis* are taller than plants of the male parent selection.
2. Plants of the new *Phalaenopsis* have larger flowers than plants of the male parent selection.
3. Plants of the new *Phalaenopsis* have white-colored flowers with yellow-colored labella whereas plants of the male parent selection have white-colored flowers with faint pink-colored stripes and red-colored labella.

Plants of the new *Phalaenopsis* can be compared to plants of *Phalaenopsis hybrida* 'Navigator', not patented. In side-by-side comparisons, plants of the new *Phalaenopsis* differ primarily from plants of 'Navigator' in flower shape as petals of plants of the new *Phalaenopsis* are free to touching whereas petals of plants of 'Navigator' are free and not touching. In addition, the curvature of the labellum is stronger in plants of the new *Phalaenopsis* than plants of 'Navigator'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Cliffhanger' grown in a container.

Figure 2:
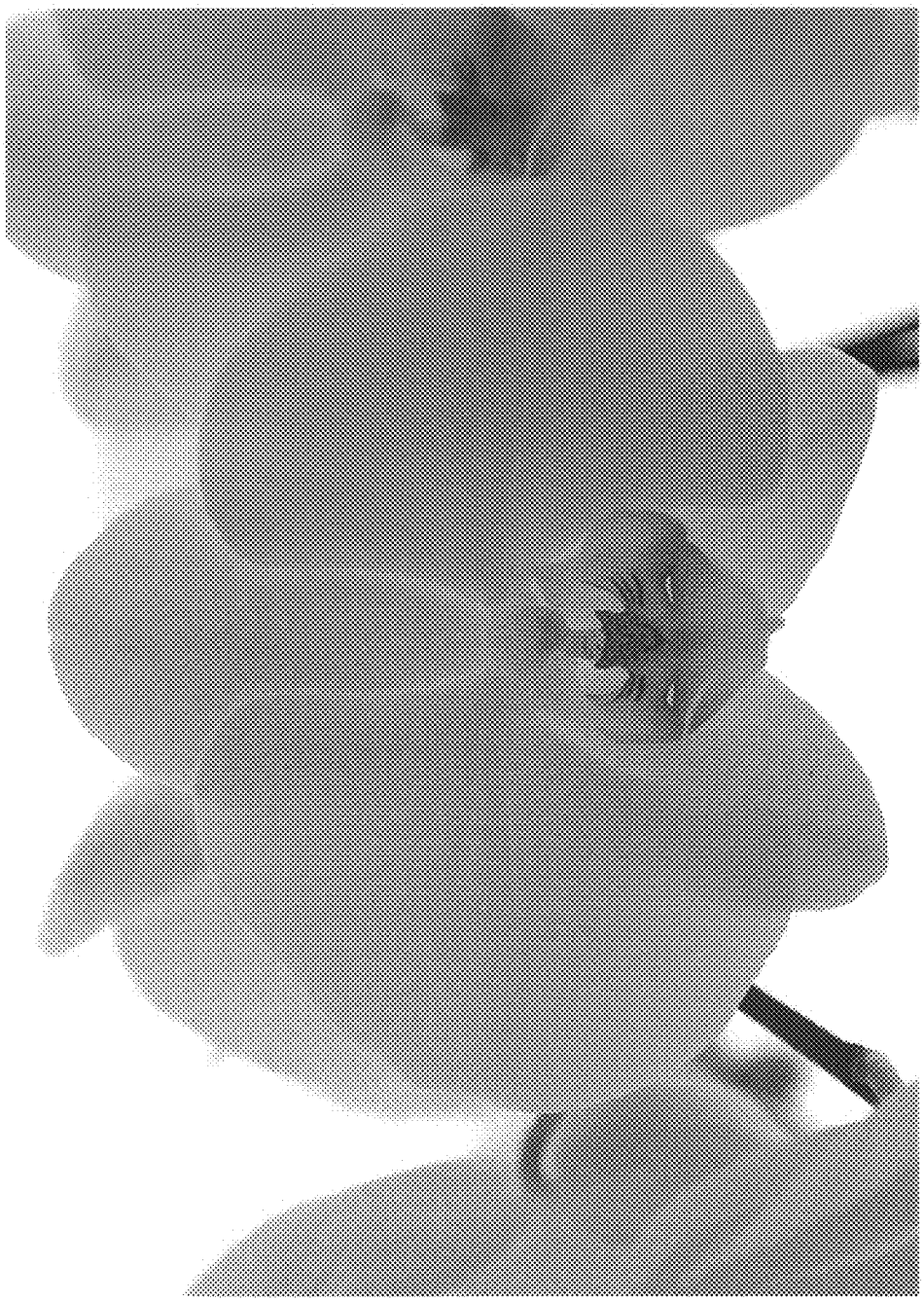

The photograph on the second sheet (FIG. 2) is a close-up view of a typical flower of 'Cliffhanger'.

DETAILED BOTANICAL DESCRIPTION

The aforementioned photographs and following observations and measurements describe plants grown during the late autumn in 10.5-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the 18 months of production, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Cliffhanger'.

Parentage:

*Female parent*.—Proprietary selection of *Phalaenopsis hybrida* identified as code number 1006336, not patented.

*Male parent*.—Proprietary selection of *Phalaenopsis hybrida* identified as code number 1006337, not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thick, fibrous; typically grey to green in color; actual color of the roots is dependent on substrate composition, water quality, fertilizer, substrate temperature and age of roots.

*Rooting habit*.—Low amount of branching; medium density.

Plant description:

*Plant form and growth habit*.—Herbaceous epiphyte; upright plant habit with typically two inflorescences per plant, each inflorescence with numerous flowers; monopodial; moderately vigorous to vigorous growth habit and moderate growth rate.

*Plant height, substrate level to top of foliar plane*.—About 18.9 cm.

*Plant height, substrate level to top of inflorescences*.—About 46.5 cm.

*Plant diameter or spread*.—About 30.4 cm.

Leaf description:

*Arrangement and quantity*.—Distichous, simple; sessile; about six leaves per plant.

*Length*.—About 18.3 cm.

*Width*.—About 7.1 cm.

*Aspect*.—Outwardly arching.

*Shape*.—Narrowly obovate to roughly oblong; slightly carinate.

*Apex*.—Unequal obtuse.

*Base*.—Sheathing. Sheath length: About 1.5 cm. Sheath width: About 1.2 cm. Sheath color: Close to 143B.

*Margin*.—Entire; not undulate.

*Texture and luster, upper and lower surfaces*.—Smooth, glabrous; slightly glossy.

*Venation pattern*.—Camptodromous.

*Color*.—Developing leaves, upper surface: Slightly darker than between NN137A and 147A. Developing leaves, lower surface: Close to 146A; towards the margins, close to between NN137A and 147A. Fully expanded leaves, upper surface: Close to NN137B; venation, close to 139A. Fully expanded leaves, lower surface: Close to 146A; towards the margins, close to NN137B; venation, close to 147B.

Inflorescence description:

*Appearance and flowering habit*.—Showy zygomorphic flowers arranged on axillary branched racemes; typically two inflorescences per plant; each inflorescence with about ten flowers; flowers face outwardly on arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about eight weeks on the plant; flowers not persistent.

*Inflorescence length* (*lowermost flower to inflorescence apex*).—About 29.9 cm.

*Inflorescence width*.—About 17.1 cm.

*Flower buds*.—Height: About 1.9 cm. Diameter: About 1.3 cm by 1.7 cm. Shape: Broadly ovate. Color: Close to between 145B and 150C; distally, slightly tinged with close to 177B.

*Flower size*.—Large, about 8.1 cm (vertical) by 9.9 cm (horizontal).

*Flower depth*.—About 3.3 cm.

*Petals, quantity and arrangement*.—Three, two lateral petals and one center petal transformed into a labellum.

*Lateral petals*.—Length: About 4.9 cm. Width: About 6.4 cm. Shape: Lunate to reniform. Apex: Rounded to shallowly retuse. Margin: Entire. Texture and luster, upper and lower surfaces: Smooth, glabrous, moderately velvety; matte. Color: When opening, upper surface: Close to NN155B. When opening, lower surface: Close to 155A; towards the margins and apex, close to NN155C. Fully opened, upper surface: Close to NN155D; venation, close to NN155D; color does not change with subsequent development. Fully opened, lower surface: Close to NN155D; towards the base, close to 157D; venation, similar to lamina colors; color does not change with subsequent development.

*Labella*.—Appearance: Three-parted with two lateral lobes and a central lobe. Length, lateral lobes: About 2.3 cm. Width, lateral lobes: About 1.7 cm. Length, central lobe: About 3 cm. Width, central lobe: About 6 mm to 22 mm. Shape, lateral lobes: Obovate to elliptic. Shape, central lobe: Deltoid. Apex, lateral lobes: Obtuse. Apex, central lobe: Emarginate with two narrow and strongly recurved cirrose tips, about 1.6 cm in length and about 1.7 mm in width. Margins, lateral lobes: Entire; coarsely undulate. Margins, central lobe: Entire. Texture and luster, upper and lower surfaces: Smooth, glabrous, moderately velvety; matte. Callosities: Located at the base of the labellum and attachment point of the lateral petals; about 5 mm in length, about 5 mm in width and about 6.5 mm in height. Color: When opening, upper surface: Lateral lobes: Close to NN155D; basal margin, close to 1A; towards the base, stripes, close to 186B. Central lobe: Close to NN155B; towards the base, close to 154B to 154C; at the base, close to 155C with radial stripes, close to 186B; edges, close to 199A; cirrose tips, close to NN155D. Callosities: Close to 12C with fine dots, close to 186B. When opening, lower surface: Lateral lobes: Close to NN155D; towards the base, close to 155D; basal margin, close to 5B; at the basal margin, close to 176B. Central lobe: Close to 157A to 157B; towards the margins and apex, close to NN155D; towards the base, close to 151D; at the base, close to 156C to 156D; edges, close to 199A; cirrose tips, close to NN155D. Fully opened, upper surface: Lateral lobes: Close to NN155D; basal margin, close to 12A; towards the base, stripes, close to 166A and 166B. Central lobe: Close to NN155B; towards the base, close to 5B; at the base, close to 155C with radial stripes, close to 166B; edges, close to 165B; cirrose tips, close to NN155D. Callosities: Close to 15B with fine dots, close to 178B. Fully opened, lower surface: Lateral lobes: Close to NN155D; towards the base, close to 155D; basal margin, close to 12B; towards the margins, close to 175D. Central lobe: Close to NN155D; towards the base, close to 151B to 151D; at the base, close to 157D; edges, close to 166D; main vein, close to 157A; cirrose tips, close to NN155D.

*Sepals*.—Quantity and arrangement: Three, one upper dorsal sepal and two lower lateral sepals. Length, dorsal sepal: About 4.8 cm. Width, dorsal sepal: About 3.8 cm. Length, lateral sepals: About 4.7 cm. Width, lateral sepals: About 3.1 cm. Shape, dorsal sepal: Broadly obovate. Shape, lateral sepals: Ovate. Apex, dorsal sepal: Obtuse. Apex, lateral sepals: Bluntly acute. Base, dorsal sepal: Truncate. Base, lateral sepals: Cuneate. Margin, dorsal and lateral sepals: Entire. Texture and luster, dorsal and lateral sepals, upper and lower surfaces: Smooth, glabrous, velvety; matte. Color, dorsal sepal: When opening, upper surface: Close to 155C. When opening, lower surface: Close to between 145C and 145D; towards the margins and apex, close to NN155A. Fully opened, upper surface: Close to NN155C. Fully opened, lower surface: Close to 157A and 157B; towards the margins and apex, close to NN155D. Color, lateral sepals: When opening, upper surface: Close to 155C; towards the base, close to 193B. When opening, lower surface: Close to 145C; towards the margins and apex, close to 145D to lighter than 145D; main vein tinged with close to 182D. Fully opened, upper surface: Close to NN155C; towards the base, close to 145C to 145D. Fully opened, lower surface: Close to 145C and close to between 145D and 150D; towards the apex and main vein, tinged with close to 186D.

*Peduncles*.—Length: About 56.2 cm. Diameter: About 5 mm. Strength: Strong. Aspect: Upright to outwardly arching. Texture and luster: Smooth, glabrous; matte. Color: Close to between 147A and 147B; fine dots, close to 146D.

*Pedicels*.—Length: About 4 cm. Diameter: About 3 mm. Strength: Moderately strong. Aspect: About 60° from peduncle axis. Texture and luster: Smooth, glabrous; matte. Color: Close to 146D; proximally, close to 146A and distally, close to 150D.

*Reproductive organs*.—Androecium: Column length: About 9 mm. Column width: About 6 mm. Column color: Close to NN155B. Pollinia quantity: Two. Pollinia diameter (per two pollinia): About 2.5 mm. Pollinia color: Close to 25B. Gynoecium: Stigma length: About 3.5 mm. Stigma width: About 4.5 mm. Stigma shape: Orbicular. Stigma color: Close to N155A. Ovary length: About 8 mm. Ovary diameter: About 1 mm. Ovary color: Close to 150B. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate temperatures ranging from about 15° to about 40° C. and are suitable for USDA Hardiness Zones 10 to 12.

It is claimed:

1. A new and distinct *Phalaenopsis* plant named 'Cliff-hanger' as illustrated and described.

* * * * *